US011957325B2

(12) United States Patent
Takegawa et al.

(10) Patent No.: US 11,957,325 B2
(45) Date of Patent: Apr. 16, 2024

(54) BIOLOGICAL TISSUE ADHESIVE NEBULIZER AND CLOGGING PREVENTION CONTAINER

(71) Applicant: KM Biologics Co., Ltd., Kumamoto (JP)

(72) Inventors: Yoshitaka Takegawa, Kikuchi (JP); Naoya Kawakami, Kumamoto (JP); Kazunori Yamanaka, Kikuchi (JP)

(73) Assignee: KM BIOLOGICS CO., LTD., Kumamoto (JP)

( * ) Notice: Subject to any disclaimer, the term of this patent is extended or adjusted under 35 U.S.C. 154(b) by 47 days.

(21) Appl. No.: 17/699,284

(22) Filed: Mar. 21, 2022

(65) Prior Publication Data

US 2022/0296227 A1  Sep. 22, 2022

(30) Foreign Application Priority Data

Mar. 22, 2021 (JP) .................................. 2021-047677
Feb. 28, 2022 (JP) .................................. 2022-029539

(51) Int. Cl.
*A61B 17/00* (2006.01)

(52) U.S. Cl.
CPC .................. *A61B 17/00491* (2013.01); *A61B 2017/00495* (2013.01); *A61B 2017/00522* (2013.01)

(58) Field of Classification Search
CPC .... A61B 17/00491; A61B 2017/00495; A61B 2017/00522
See application file for complete search history.

(56) References Cited

U.S. PATENT DOCUMENTS

| 4,359,049 A | 11/1982 | Redl et al. |
| 5,020,694 A * | 6/1991 | Pettengill ............. B65D 81/325 |
| | | 401/35 |
| 5,582,596 A * | 12/1996 | Fukunaga ........ A61B 17/00491 |
| | | 604/82 |

(Continued)

FOREIGN PATENT DOCUMENTS

| JP | 3-47609 | 10/1991 |
| JP | 7-184952 | 7/1995 |

(Continued)

OTHER PUBLICATIONS

Tidrick R.T., Warner E.D., "Fibrin fixation of skin transplants", Surg., 1944, 15:90-5.

(Continued)

*Primary Examiner* — Mohamed G Gabr
(74) *Attorney, Agent, or Firm* — Wenderoth, Lind & Ponack, L.L.P.

(57) ABSTRACT

A nebulizer capable of reliably intermittently applying a biological tissue adhesive is provided. A biological tissue adhesive nebulizer includes a first tube 30 for injecting a first solution containing a first component, and a second tube 30 for injecting a second solution containing a second component that promotes clot formation of the first component. The first solution injected from the first tube and the second solution injected from the second tube are mixed to generate and spray a biological tissue adhesive. A partition wall 34 is provided between a distal end 31 of the first tube and a distal end 31 of the second tube.

7 Claims, 9 Drawing Sheets

(56) References Cited

U.S. PATENT DOCUMENTS

| 2014/0263749 | A1* | 9/2014 | Davis | B01F 33/50112 |
|---|---|---|---|---|
| | | | | 239/403 |
| 2015/0216516 | A1* | 8/2015 | Steffen | A61B 17/00491 |
| | | | | 604/290 |
| 2018/0361065 | A1* | 12/2018 | Trezza | A61M 5/31511 |

FOREIGN PATENT DOCUMENTS

| JP | 2001-157716 | 6/2001 |
|---|---|---|
| JP | 3172382 | 12/2011 |
| WO | 94/07420 | 4/1994 |

OTHER PUBLICATIONS

Web site of general incorporated association Japan Blood Products Association: http://www.ketsukyo.or.jp/plasma/fibrin-paste/fib_02.html (confirmed on Dec. 1, 2020) with its English translation.
Web site of general incorporated association Japan Blood Products Association: http://www.ketsukyo.or.jp/plasma/fibrin-paste/fib_05_03.html (confirmed on Dec. 1, 2020) with its English translation.
CSL Behring Product Information List Beriplast P Combi-Set Tissue adhesion "Auxiliary Equipment Handbook" Web site: https://csl-info.com/products/beriplast05 (confirmed on Dec. 1, 2020) with its English translation.

* cited by examiner

BIOLOGICAL TISSUE ADHESIVE NEBULIZER AND CLOGGING PREVENTION CONTAINER

BACKGROUND OF THE INVENTION

Field of the Invention

The present invention relates to a biological tissue adhesive nebulizer that sprays and applies a biological tissue adhesive. The present invention also relates to a clogging prevention container used together with a biological tissue adhesive nebulizer.

Description of the Related Art

In surgery, suturing with a thread has been performed in order to bond a tissue since a long time ago, but there have been problems that a wound occurs due to a needle hole in the tissue for suturing, the adhesion of the tissue takes many days, and the thread is required to be removed after the tissue adhesion. In order to solve these problems, studies using fibrin for adhesion enhancement of suture started in around 1910. The clinical application of the current fibrin glue preparation was first carried out in 1944 by Tidrick R T et al using two components of fibrinogen and thrombin at the time of skin transplantation, but the adhesive force was weak, and the effect was insufficient (Tidrick R T, Warner E D. Fibrin fixation of skin transplants. Surg. 1944; 15:90-5).

Then, in 1970, when protein purification technology progressed and a solution of fibrinogen or thrombin at a high concentration can be separated, blood coagulation factor XIII that strengthens the network of fibrin after the reaction of both fibrinogen and thrombin was also discovered (WEB site of general incorporated association Japan Blood Products Association: http://www.ketsukyo.or.jp/plasma/fibrin-paste/fib_02.html (confirmed on Dec. 1, 2020)). With the development of these technologies, Tisseel (registered trademark: Immuno AG), a fibrin glue preparation that was developed for the first time in the world, was developed in 1978, and Beriplast (registered trademark) P (CSL Behring K.K.) was released in 1988 and BOLHEAL (registered trademark: KM Biologics Co., Ltd.) was released in 1991 in Japan. The fibrin glue is composed of four components, liquid A obtained by dissolving a fibrinogen (containing blood coagulation factor XIII) freeze-dried powder in a fibrinogen solvent (containing aprotinin) is prepared, and liquid B obtained by dissolving a thrombin freeze-dried powder in a thrombin solvent (containing calcium chloride) is prepared. By mixing the liquid A and the liquid B at the adhesion face of the tissue, the liquid A and the liquid B are used for adhesion and closure of the tissue. At the time of release, the "multilayer method" in which one solution of the liquid A or the liquid B was applied to the application site and the other solution was applied, alternately, or the "mixing method" in which the liquid A and the liquid B were mixed while being simultaneously applied was mainly used. However, the multilayer method has a problem that most of the fibrinogen solvent flows down before the fibrin gel is formed, and the mixing method has a problem that the formed fibrin gel is non-uniform. Therefore, these methods have limited efficacy of the fibrin glue preparation.

Not only in Japan but also in the world, the demand for fibrin glue preparations in the market has gradually expanded since the release, and as an aid, there is development of applicators. As described above, the fibrin glue is obtained by mixing the fibrinogen solvent as the liquid A with the thrombin solvent as the liquid B, and the development of a gas spray device that uniformly mixes the fibrinogen solvent and the thrombin solvent at the target site made it possible to produce a strong and uniform fibrin gel, and it was highly evaluated in the market that the convenience and effectiveness were improved (JP 03-047609 A and WO 1994/07420 A). Even after the development of this gas type spray device, along with the sequential development of an improved spray nozzle, a spray nozzle that can be used under a thoracoscope (JP 2001-157716 A), a micro dropping device for otorhinolaryngology (JP H07-184952 A), and the like, fibrin glue preparations have become important biological tissue adhesives in surgical operations even after about 30 years have passed since the release in Japan.

The application of a fibrin glue preparation in Japan is "adhesion/closure of tissues", but it is widely used in various areas.

The primary use applications are reinforcement of suture sites, hemostasis in damaged tissue, prevention of air and fluid leakage, supplementation and coverage of tissue defects, and the like. Main clinical fields are neurosurgery, respiratory surgery, cardiovascular surgery, obstetrics and gynecology, and digestive surgery, and recently, include oral surgery and the like (WEB site of general incorporated association Japan Blood Products Association: http://www.ketsukyo.or.jp/plasma/fibrin-paste/fib_05_03.html (confirmed on Dec. 1, 2020)).

SUMMARY OF THE INVENTION

Fibrin glue preparations have become important in surgery, and as a background thereof, contribution to improvement and progress of applicators is significant. Specifically, a gas type spray using compressed air or the like has been useful in medical sites for many years from the viewpoint of uniform application and good mixing of both liquids. However, it has been a conventional problem that clogging frequently occurs at the spray tip due to the properties of the fibrin glue preparation, and in recent years, sprays with measures for clogging have been released from various companies. In Beriplast (registered trademark) P Combi-Set Tissue adhesion (CSL Behring K.K.), the "BeriP short tip end clogging prevention type" has been developed, and a triple bellows pump system pulls back residual liquid at the tip of a nozzle, which causes liquid sagging, so that liquid A and liquid B are not mixed, and a U-shaped double-slit-shaped tip nozzle prevents adhesion and accumulation of a liquid medicine, which causes tip clogging (CSL Behring Product Information List Beriplast (registered trademark) P Combi-Set Tissue adhesion "Auxiliary Equipment Handbook" WEB site: https://csl-info.com/products/beriplast05 (confirmed on Dec. 1, 2020)). In BOLHEAL (registered trademark) tissue adhesion (KM Biologics Co., Ltd.), a "spray dock holder type" has been developed. With this type, a container (dedicated stand) containing physiological saline is provided with a tip of the applicator spray, and the liquid A and the liquid B attached to the spray tip causing clogging of the tip are diluted with physiological saline, so that the two liquids are not solidified at the tip, and at the same time, the two liquids are prevented from being solidified due to drying at the spray nozzle tip (JP 3172382).

The "BeriP short tip end clogging prevention type" has a problem in terms of its clogging prevention effect, and the "spray dock holder type" has a high clogging prevention effect, but it is an obstacle in a limited installation space of a surgical instrument, and therefore, it cannot completely satisfy the medical needs. From the above, in the applicator spray of the fibrin glue preparation, a device having both clogging prevention and installation convenience is desired. In addition, in a spray having a long tip for endoscopic surgery, it is described that the "BeriP long type" has a clogging prevention function, but the effect is low, and the occurrence of clogging has not been theoretically solved. The "end spray 32 cm straight type" for BOLHEAL has a long length to the tip of the spray, and clogging is likely to occur. When spraying is stopped once and then sprayed again, clogging occurs with high probability, and thus there is a possibility that spraying cannot be performed a plurality of times.

In addition, the fibrin glue preparation is used for reinforcement of a suture site, hemostasis in damaged tissue, prevention of air and body fluid leakage, and supplementation and covering of a tissue defect in a surgical operation. There is a case where the liquid A and the liquid B are sprayed and mixed at a distance close to the target tissue to be adhered, and in the stage before spraying or after spraying, it may theoretically occur that the tip of the applicator spray comes into contact with the target tissue during surgery and damages the tissue. Specifically, in endoscopic surgery, the distance between the spray tip and the organ tends to be short, and it is difficult to measure the distance from the two-dimensional image, so that the risk increases.

As a result of intensive studies to solve the above problems, the present inventors have found, in a conventional applicator spray of a fibrin glue preparation, a partition wall for separating two liquid spray ports of the liquid A and the liquid B for preventing clogging of the tip, and an appropriate tip structure that does not damage tissues.

Further, a small clogging prevention container, containing a solution, such as physiological saline, attached to the applicator spray tip has been found.

Specifically, an embodiment of a biological tissue adhesive nebulizer according to the present invention includes a first tube (30) for injecting a first solution containing a first component; and a second tube (30) for injecting a second solution containing a second component that promotes clot formation of the first component, where the first solution injected from the first tube (30) and the second solution injected from the second tube (30) are mixed to generate and spray a biological tissue adhesive, wherein a partition wall (34) is provided between a distal end (31) of the first tube (30) and a distal end (31) of the second tube (30).

In another embodiment of the present invention, the biological tissue adhesive nebulizer (10) includes a spray head (18), wherein the spray head (18) has a hollow housing (21), wherein the housing (21) has a center axis (20) extending from a proximal side to a distal side and a proximal portion (22) and a distal portion (25) located on a proximal side and a distal side of the center axis (20), respectively, wherein the distal portion (25) has a first through hole (29) and a second through hole (29) formed along a first axis (26) and a second axis (26), respectively, extending in parallel from the proximal side toward the distal side and communicating an inside (27) and an outside (28) of the housing (21), wherein the first tube (30) and the second tube (30) are inserted into the first through hole (29) and the second through hole (29), respectively, and protrude from an end face (33) of the distal portion (25), and wherein the partition wall (34) is provided between the first through hole (29) and the second through hole (29) at the end face (33) of the distal portion (25).

In another embodiment of the present invention, the first axis (26) of the first through hole (29) and the second axis (26) of the second through hole (29) are parallel to the center axis (20).

In another embodiment of the present invention, a plane including the first axis (130) of the first through hole (131) and the second axis (130) of the second through hole (131) obliquely intersects with the tenter axis (20).

In another embodiment of the present invention, an inner diameter of the first through hole (29) is larger than an outer diameter of the first tube (30), and a first gas injection hole (32) is formed around the first tube (30) inserted into the first through hole (29), wherein an inner diameter of the second through hole (29) is larger than an outer diameter of the second tube (30), and a second gas injection hole (32) is formed around the second tube (30) inserted into the second through hole (29), wherein a sterile gas supply pipe (35) is connected to the inside (27) of the housing (21), and wherein a sterile gas supplied from the sterile gas supply pipe (35) to the inside (27) of the housing (21) is injected from the first gas injection hole (32) formed between an inner face of the first through hole (29) and an outer face of the first tube (30) and the second gas injection hole (32) formed between an inner face of the second through hole (29) and an outer face of the second tube (30).

In another embodiment of the present invention, the partition wall (34) extends along a plane perpendicular to a plane parallel to the first axis (26) and the second axis (26) and including the first axis (26) and the second axis (26).

In another embodiment of the present invention, one end portion or the other end portion or both end portions of the partition wall (34) in a first direction (z direction) orthogonal to a plane including the first axis (26) and the second axis (26) have a pair of protective walls (37) extending in a second direction away from the partition wall (34) along the end face (33).

Another embodiment of the present invention is a container for use with the biological tissue adhesive nebulizer according to the above-described embodiment, wherein the container has a mouth shape detachably attachable to a terminal portion of the housing, and accommodates physiological saline therein.

According to the biological tissue adhesive nebulizer of the embodiment of the present invention, since the distal end (31) of the first tube (30) and the distal end (31) of the second tube (30) are separated from each other by the partition wall (34) provided therebetween, the solutions leaking from the first and second tubes are not mixed and coagulated near the distal ends of the first and second tubes when spraying is interrupted. In addition, when there is a difference in viscosity between the two liquids of the biological tissue adhesive, it is conceivable that a phenomenon occurs in which a liquid having higher viscosity is sucked up into the tube (30) through which a liquid having lower viscosity passes due to a difference in liquid passage resistance between the two liquids, and coagulation/occlusion occurs in the tube (30). However, according to the embodiment of the present invention, it is possible to prevent mixing of the two liquids at the end face (33) by the partition wall (34) and to prevent the coagulation/occlusion. Therefore, it is possible to reliably and quickly resume the spraying of the biological tissue adhesive even after the interruption.

BRIEF DESCRIPTION OF THE DRAWINGS

FIG. 13(a) is a view illustrating a mode in which a protective wall is formed on the entire periphery of a distal portion end face edge, FIG. 13(b) is a view illustrating a mode in which a protective wall is formed in a range of 45 degrees from the partition wall, and FIG. 13(c) is a view illustrating a mode in which a protective wall is formed in a range of 22.5 degrees from the partition wall.

DETAILED DESCRIPTION OF THE PREFERRED EMBODIMENTS

Hereinafter, preferred embodiments of the present invention will be described with reference to the accompanying drawings.

First Embodiment

Figure 1:
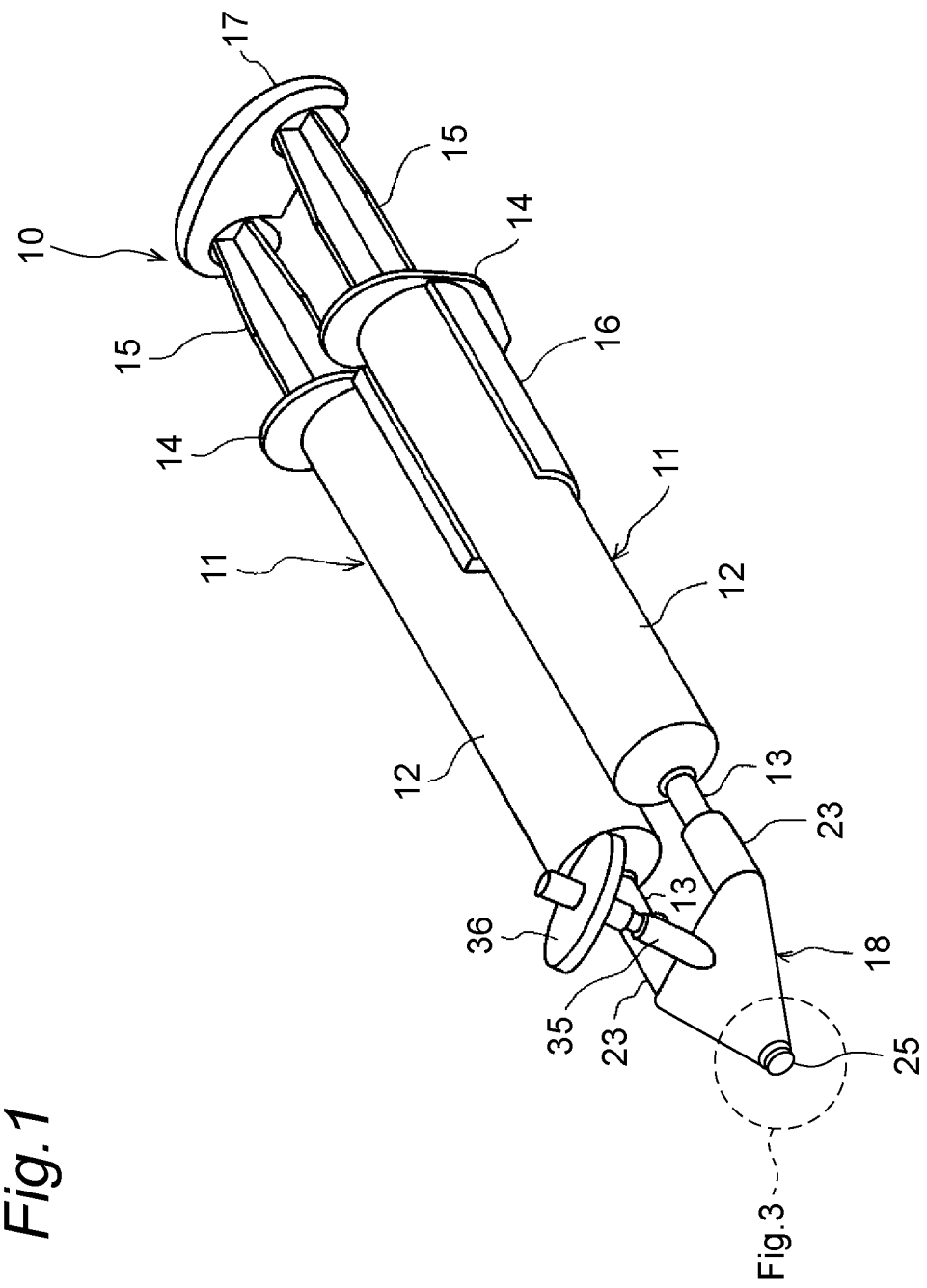
FIG. 1 is a perspective view of a biological tissue adhesive nebulizer according to a first embodiment of the present invention.

FIG. 1 illustrates a biological tissue adhesive nebulizer (hereinafter, it is referred to as a "nebulizer") 10 according to the first embodiment. The nebulizer 10 has two syringes 11 each containing two solutions described below. Each syringe 11 has a hollow cylindrical barrel 12 that contains a solution to be described later. The barrel 12 has a nozzle 13 integrally provided at the distal end of the barrel 12 and a flange (finger grip) 14 integrally provided at the proximal end of the barrel 12. The proximal end of the barrel 12 is open, and a plunger rod 15 is inserted through the opening. The two syringes 11 are disposed in parallel as illustrated, with the proximal side of the barrel 12 being held by a barrel holder 16 and the distal side being held by a spray head 18. The proximal end of the plunger 15 is held by a plunger holder 17. Therefore, when a plunger 15 is moved from the proximal side to the distal side while pressing the plunger holder 17 in a state where the solution is stored in each of the two syringes 11, the solution stored in each syringe 11 is simultaneously discharged from the nozzle 13.

Figure 2:
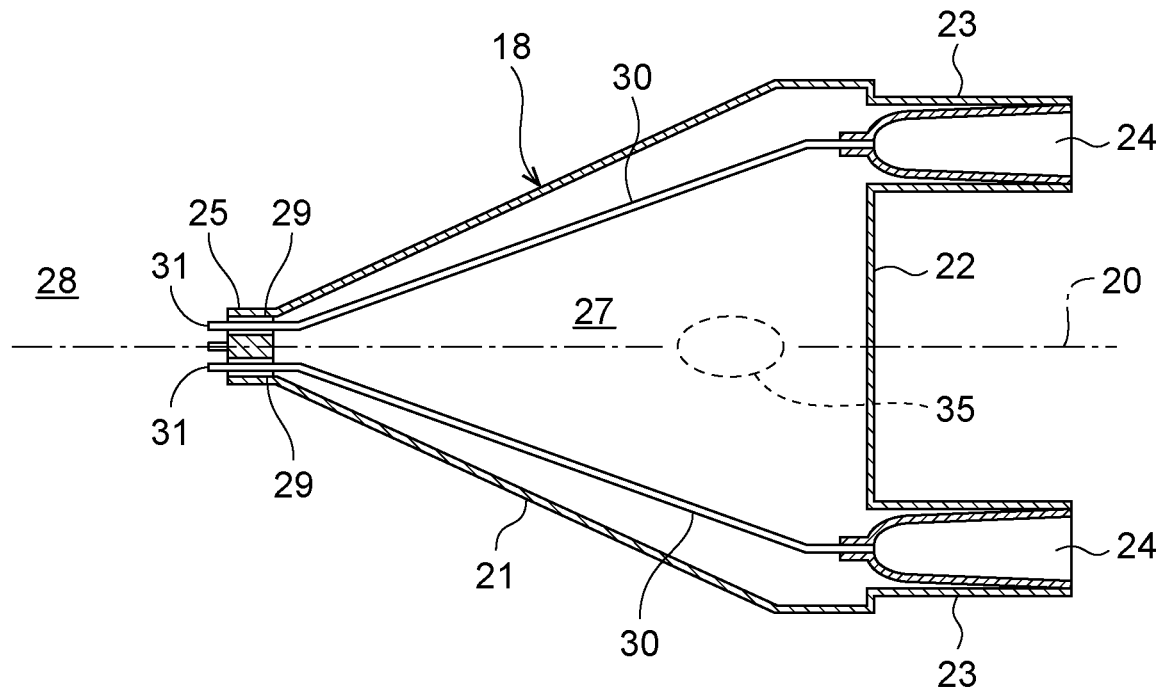
FIG. 2 is a transvers cross-sectional view of a spray head of the nebulizer illustrated in FIG. 1.

The spray head 18 is detachably attached to the nozzle 13 of the syringe 11. In the first embodiment, as illustrated in FIG. 2, the spray head 18 has a substantially quadrangular frustum shaped hollow housing 21 whose cross section gradually decreases from a proximal side (right side in the figure) toward a distal side (left side in the figure) along a center axis 20.

The proximal portion 22 of the housing 21 is provided with a pair of hollow cylindrical syringe coupling portions 23 symmetrical about and parallel to the center axis 20. A nozzle insertion barrel 24 that receives the nozzle 13 of the syringe 11 is fixed to the inside of the syringe coupling portion 23, and a gap between an inner face of the syringe coupling portion 23 and an outer face of the nozzle insertion barrel 24 are sealed. The nozzle insertion barrel 24 has an inner face shape corresponding to the outer face shape of the nozzle 13 of the syringe 11. Therefore, in a state where the nozzle 13 of the syringe 11 is inserted into the nozzle insertion barrel 24 of the spray head 18, a gap between the outer face of the nozzle 13 and the inner face of the nozzle insertion barrel 24 is sealed.

In the first embodiment, the distal portion 25 of the housing 21 is formed in a substantially cylindrical shape, and a pair of through holes (a first through hole and a second through hole) 29 for communicating the inside (internal space) 27 and the outside (external space) 28 of the housing 21 is formed at the distal portion 25 along a pair of axes 26 symmetrical about and parallel to the center axis 20.

A pair of tubes 30 is disposed in the inside 27 of the housing 21. A proximal end of the tube 30 is connected to a distal end of the nozzle insertion barrel 24, and a solution pushed out from the nozzle 13 of the syringe 11 is supplied to the tube 30. The distal side of the tube 30 is inserted into the through hole 29. In the first embodiment, the tube distal end 31 protrudes from the through hole 29 by a predetermined length.

The inner diameter of the through hole 29 is designed to be slightly larger than the outer diameter of the tube 30, and a gap (sterile gas injection hole) 32 (see FIG. 4) for communicating the inside 27 and the outside 28 of the housing 21 is formed between the inner face of the through hole 29 and the outer face of the tube 30.

Figure 3:
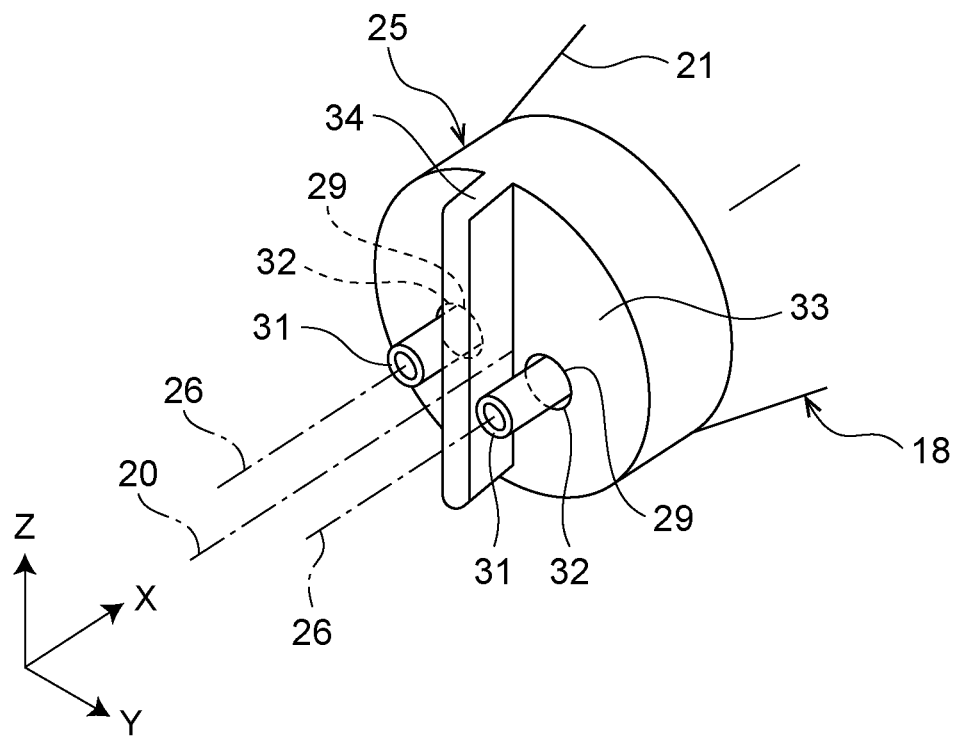
FIG. 3 is an enlarged perspective view of a distal portion of the spray head illustrated in FIG. 2.
Figure 4:
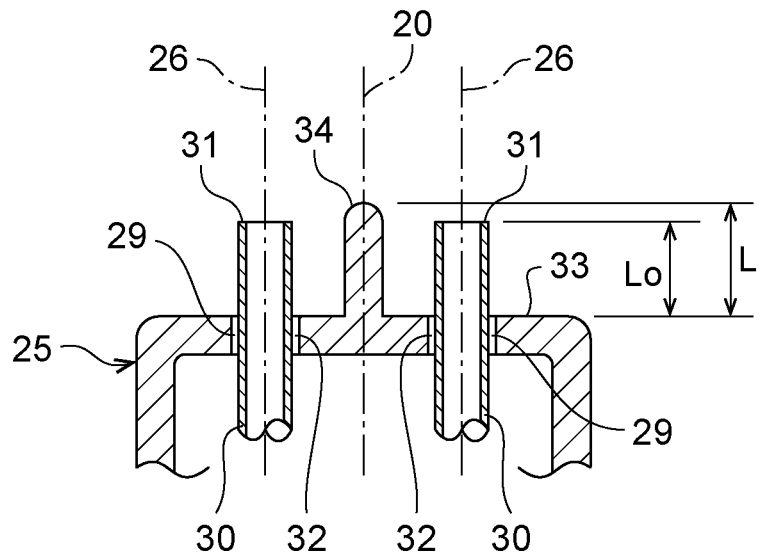
FIG. 4 is an enlarged cross-sectional view of a distal portion of the spray head illustrated in FIG. 2.
Figure 5:
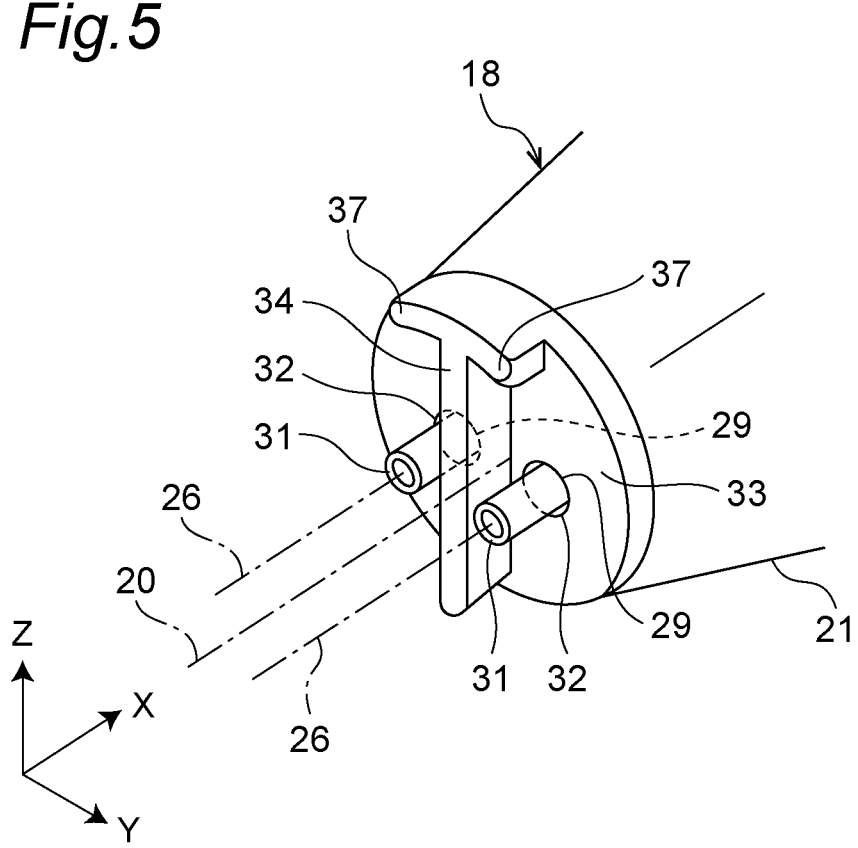
FIG. 5 is an enlarged perspective view of the spray head distal portion in another form.

As illustrated in FIGS. 3 and 4, the end face 33 of the housing distal portion 25 has a plate-like partition wall 34 in the middle between the through holes 29. The partition wall 34 extends along a plane orthogonal to a plane including the axes 26 of the two through holes 29, that is, in a direction (first direction, z direction) orthogonal to two directions (x, y direction), that is a direction (x direction) of the center axis 20 and a direction (y direction) orthogonal to the two axes 26. The height of the partition wall 34, that is, the amount of protrusion L from the end face 33 is slightly larger than the amount of protrusion $L_0$ from the end face 33 of the tube 30. However, the height L of the partition wall 34 may be the same as the amount of protrusion $L_0$ of the tube 30 or smaller than the amount of protrusion $L_0$ of the tube 30.

Returning to FIG. 2, a sterile gas supply pipe 35 is connected to the upper face or the lower face of the housing 21. The distal end of the sterile gas supply pipe 35 opens to the inside 27 of the housing 21. On the other hand, referring back to FIG. 1, the proximal end of the sterile gas supply pipe 35 is connected to a sterile gas supply source (not illustrated) via a sterilization filter 36. Therefore, the sterile gas supplied from the sterile gas supply source is sterilized by the sterilization filter 36, then supplied to the inside 27 of the housing 21 via the sterile gas supply pipe 35, and injected from the periphery of the tube 30 via the gap (sterile gas injection hole) 32 of the distal portion 25.

When the biological tissue adhesive is sprayed by the nebulizer 10 configured as described above, a solution (first solution) containing blood coagulation factor XIII and fibrinogen is accommodated in one syringe 11, and a thrombin-containing solution (second solution) is accommodated in the other syringe 11. For the syringe 11 containing each solution, the proximal side of the syringe barrel 12 is held by the barrel holder 16, and both the plunger rods 15 are held by the plunger holder 17. The nozzle 13 of the syringe 11 is inserted into the nozzle insertion barrel 24 of the spray head 18, and the syringe 11 and the spray head 18 are connected. Then, the sterile gas supply pipe 35 of the spray head 18 is connected to a gas supply source via a tube (not illustrated).

When the solution is sprayed using the nebulizer 10 assembled in this manner, the gas supplied from the sterile gas supply source is sterilized by the sterilization filter 36, and then injected from the gap (gas injection hole) 32 through the sterile gas supply pipe 35 via the inside 27 of the spray head 18.

In this state, when the plunger holder 17 is pushed to move the plunger rod 15 to the distal side, the solution contained in the syringe 11 is sent from the nozzle 13 of the syringe 11 to the tube 30, and is injected from the distal end (nozzle) 31 of the tube 30. The injected solutions are atomized by the sterile gas injected from the periphery of the tube 30, mixed in the atmosphere, and applied to a target affected area.

During surgery, the ejection of the solution occurs intermittently, and the ejection and subsequent ejection may take minutes to tens of minutes. In this case, when there is no partition wall, the fibrinogen solvent and the thrombin solvent leaking from the distal end of the tube 30 come into contact with each other on the end face 33 of the housing distal portion 25 and coagulate, and block the tip opening of the tube 30 or clog in the gap (gas injection hole) 32. However, in the above-described embodiment, since the two tubes 30 are separated by the partition wall 34, the two solutions are not mixed on the end face 33. Therefore, according to the first embodiment, the tube 30 and the gap (gas injection hole) 32 are prevented from being clogged due to the two solutions mixing with each other and coagulating at the distal end of the spray head 18. Therefore, according to the nebulizer 10 of the first embodiment, the solution is reliably sprayed even after the interruption.

In the first embodiment described above, the shape of the partition wall 34 can be appropriately modified. For example, as illustrated in FIG. 5, one end (end in the z direction) of the partition wall 34 may be extended in two directions (the y direction and a direction opposite to it) away from the partition wall 34 to form a pair of protective walls (partition wall guard) 37. Alternatively, as illustrated in FIG. 6, both ends (an end in the z direction and an end opposite to it) of partition wall 34 may be extended in two directions (the y direction and the opposite direction) away from partition wall 34 to form two pairs of protective walls 37 and 38. According to these forms, it is possible to prevent contact between the upper end portion or the lower end portion of the partition wall 34 and the biological tissue.

In the embodiment illustrated in FIG. 6, the length of one protective wall 37 appearing on the upper side of the diagram (the length from the partition wall 34) is the same as the length of the other protective wall 38 appearing on the lower side of the diagram, but the length of one protective wall 37 may be larger or smaller than the length of the other protective wall 38.

In addition, in the case of the embodiment illustrated in FIG. 6, an annular protective wall may be formed by extending and coupling the upper protective wall 37 and the lower protective wall 38 toward each other along the edge of the end face 33. However, as illustrated in FIG. 7, it is preferable to provide an appropriate distance (an opening distance H or an opening angle θ) between the end of one protective wall 37 and the end of the other protective wall 38 so that the solution does not stay on the end face 33.

Second Embodiment

FIGS. 8 and 9 illustrate a spray head 118 according to the second embodiment instead of the spray head 18 of the first embodiment described above. As illustrated, the spray head 118 of the second embodiment differs from the spray head 18 of the first embodiment in the structure of the distal portion.

Specifically, a distal portion 125 of the spray head 118 of the second embodiment has an elongated extension 126 extending along the center axis 20. The length of the extension 126 is, for example, about 3 cm to about 30 cm. The extension 126 is formed by a rigid hollow tube so that the illustrated shape can be stably maintained. A proximal end of the extension 126 is open to the inside 27 of the housing 21, and the inside 127 of the extension 126 communicates with the inside 27 of the housing 21.

The distal end of the extension 126 is closed by an end wall 128. In the second embodiment, the end wall 128, particularly a distal end face 129 of the end wall 128, is an oblique face with respect to the center axis 20. The end wall 128 has through holes 131 that are on a plane obliquely intersecting the center axis 20 and that are along two axes 130 that appear symmetrical about and parallel to the center axis 20 when viewed from above (when viewed from a direction opposite to the z direction), and a distal end 132 of the tube 30 extending from the inside 27 of the housing 21 to the inside 127 of the extension 126 protrudes from each of the through holes 131. In the second embodiment, the axis 130 is oriented in a direction substantially orthogonal to the oblique end face 129 (the y' direction illustrated in FIG. 9(*b*)).

As in the first embodiment, the inner diameter of the through hole 131 is designed to be larger than the outer diameter of the tube 30, and a gap (sterile gas injection hole) 133 for communicating the inside 127 and the outside 28 of the extension 126 is formed between the inner face of the through hole 131 and the outer face of the tube 30.

The end face 129 of the extension end wall 128 has a plate-shaped partition wall 134 in the middle between the through holes 131. The partition wall 134 extends along the end face 129 and along a plane orthogonal to the plane including the two axes 130 (the z' direction illustrated in FIG. 9(*b*)). The height of the partition wall 134, that is, the amount of protrusion L of the extension 126 from the end face 129 is slightly larger than the amount of protrusion $L_0$ of the tube 30 from the end face 129. However, the height L of the partition wall 134 may be the same as the amount of protrusion $L_0$ of the tube 30 or smaller than the amount of protrusion $L_0$ of the tube 30.

According to the spray head 118 of the second embodiment configured as described above and the nebulizer including the spray head 118, the gas supplied from the sterile gas supply source passes through the sterilization filter 36, the sterile gas supply pipe 35, and the inside 27 of the spray head 118, and then is injected from the gap (gas injection hole) 133 via the inside 127 of the extension 126.

Meanwhile, the solution sent from the syringe 11 to the tube 30 is ejected from the distal end (nozzle) 132 of the tube 30. The injected solutions are atomized by the sterile gas injected from the periphery of the tube 30, mixed in the atmosphere, and applied to a target affected area.

As in the first embodiment, also in the second embodiment, since the two tubes 30 are separated by the partition wall 134, a solution leaking from one tube 30 does not mix with a solution leaking from the other tube 30 at the time of interruption. Therefore, according to the second embodiment, the tube 30 and the gap (gas injection hole) 133 are prevented from being clogged due to the two solutions mixing with each other and coagulating at the distal end of the spray head 118. Therefore, according to the nebulizer of the embodiment, the solution is reliably sprayed even after the interruption.

Figure 9:
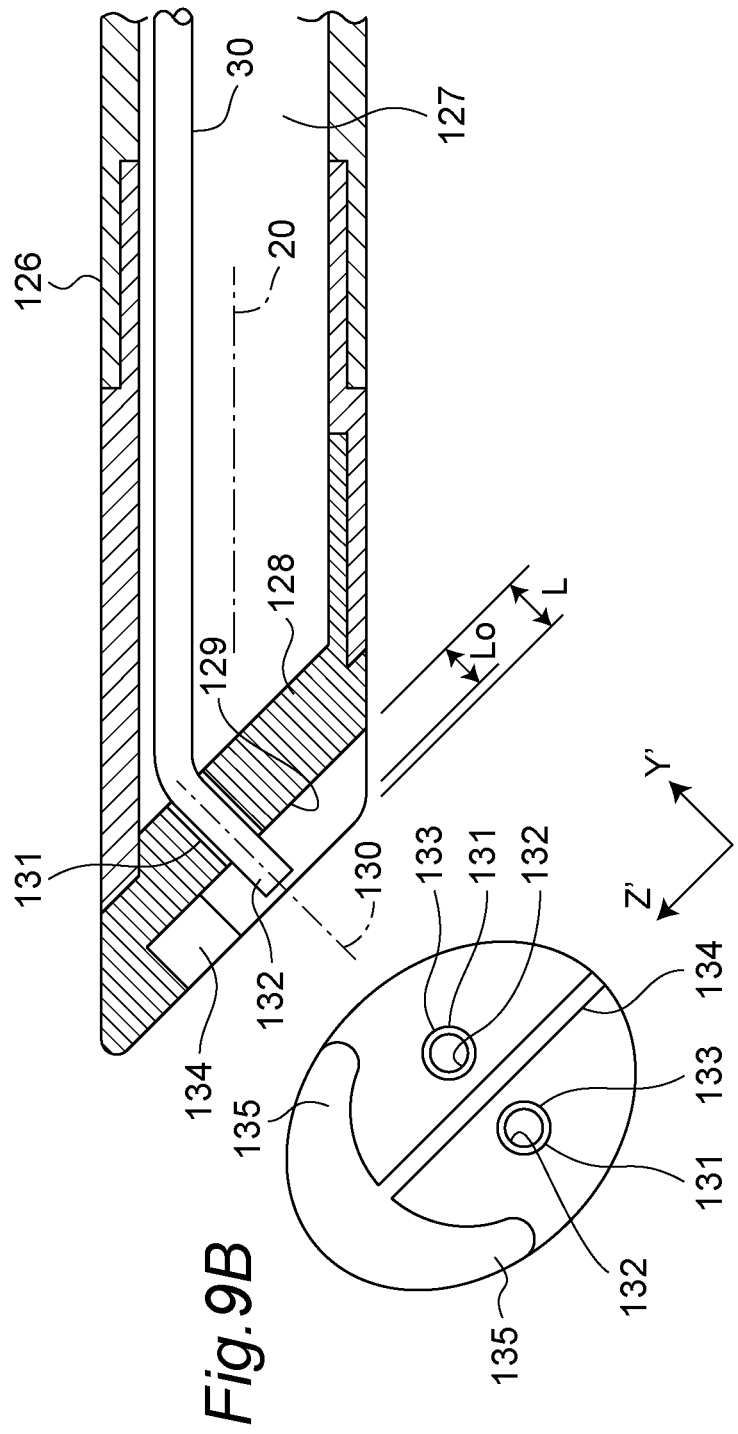
FIG. 9(a) is an enlarged cross-sectional view of a distal portion of the spray head illustrated in FIG. 8.
FIG. 9(b) is an end face view of the spray head illustrated in FIG. 9(a)

As in the first embodiment described above, the shape of the partition wall 134 can be appropriately modified. For example, as illustrated, one end (for example, the end portion in the z' direction in FIG. 9(b)) of partition wall 134 may be extended in two directions away from partition wall 134 (the y' direction and the direction opposite to it) to form a pair of protective walls 135.

Figure 6:
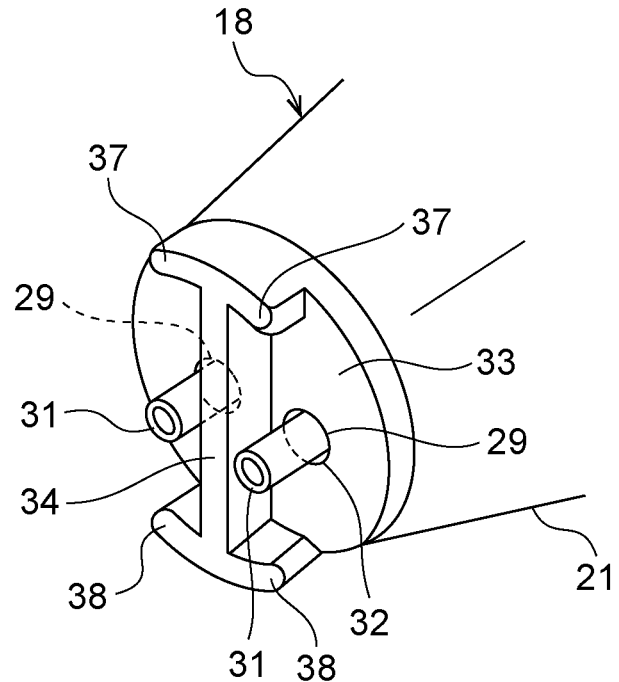
FIG. 6 is an enlarged perspective view of a spray head distal portion in another form.
Figure 7:
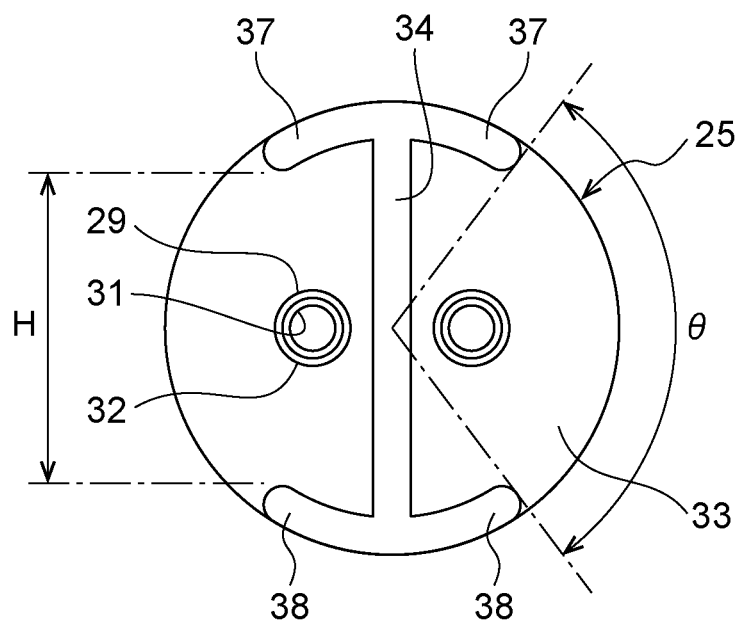
FIG. 7 is a front view of the spray head distal portion illustrated in FIG. 6.
Figure 8:
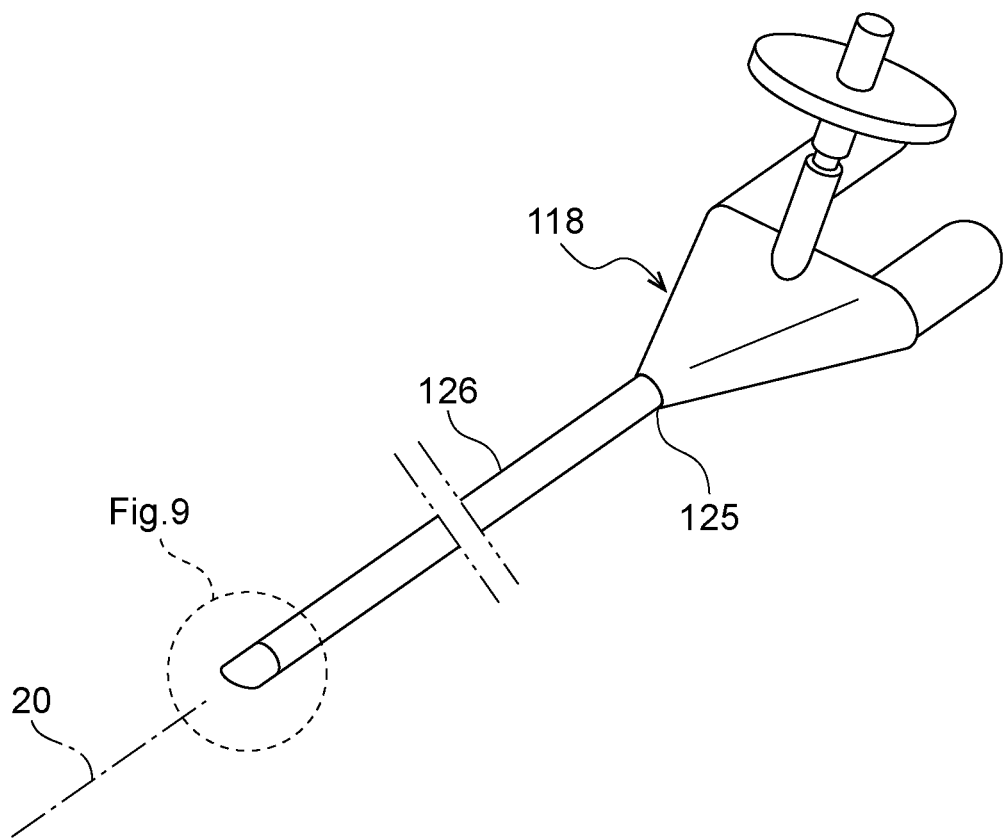
FIG. 8 is a perspective view of a spray head attached to a biological tissue adhesive nebulizer according to a second embodiment of the present invention.

As in the forms illustrated in FIGS. 6 and 7, both ends (an end in the z' direction and an end opposite to it) of partition wall 134 may be extended in two directions (the y' direction and the opposite direction) away from partition wall 134 to form two pairs of protective walls. According to the embodiment, it is possible to prevent contact between the upper end portion or the lower end portion of the partition wall 134 and the biological tissue.

In addition, the length of the upper protective wall (the length from the partition wall 134) and the length of the lower protective wall may be the same, or the length of the upper protective wall may be larger or smaller than the length of the lower protective wall.

Furthermore, an annular protective wall may be formed by extending and coupling the upper protective wall and the lower protective wall toward each other along the edge of the end face 129. However, it is preferable to provide an appropriate distance between the end of the upper protective wall and the end of the lower protective wall so that the solution does not stay on the end face 129.

In the second embodiment described above, the end wall 128 and the end face 129 of the extension 126 are formed obliquely with respect to the center axis 20, and the axis 130 of the through hole 131 is oriented obliquely with respect to the center axis 20. However, the end wall and the end face may be oriented in a direction orthogonal or substantially orthogonal to the center axis 20, and the axis of the through hole may be oriented in a direction parallel or substantially parallel to the center axis. Specifically, a through hole parallel or substantially parallel to the center axis 20 may be formed in an oblique end wall, or an oblique through hole may be formed in an end wall directed in a direction orthogonal to the center axis 20.

OTHER EMBODIMENTS

Figure 10:
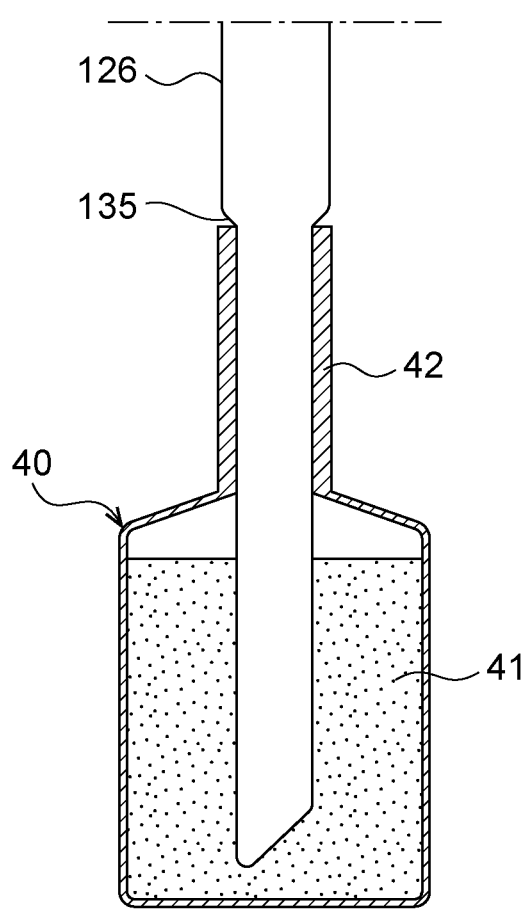
FIG. 10 is an enlarged cross-sectional view of a distal end of a spray head and a small clogging prevention container attached thereto.

In order to prevent clogging during the interruption, as illustrated in FIG. 10, a small clogging prevention container 40 that can be attached to the distal portion 25 (see FIGS. 1 and 2) of the spray head or the extension 126 may be provided so that during the interruption of spraying, the distal portion 25 of the spray head or the distal portion of the extension 126 is immersed in a solution (such as physiological saline) 41 contained in a container 40. In this case, it is desirable that the distal portion 25 of the spray head or the extension 126 do not contact the bottom face of the container 40.

The container 40 is preferably shaped such that a container mouth 42 has a shape corresponding to the distal portion of the spray head or the distal portion of the extension 126. The gap between the outer face of the distal portion 25 of the spray head or the distal portion of the extension 126 and the inner face of the container mouth 42 is preferably determined such that surface tension of the solution prevents leakage of the solution. In this case, even when the spray head immersed in the container 40 and the container 40 are turned sideways, the solution does not leak.

A step or stopper (engaging portion) 135 is preferably formed at the distal portion of the spray head or the distal portion of the extension 126 to ensure that the distal portion 25 of the spray head or the distal portion of the extension 126 is immersed in the solution 41 with the step 135 contacting the end of a container mouth (engaged portion) 42. In this case, it is desirable that the distal portion 25 of the spray head does not contact the bottom face of the container 40.

Figure 11:
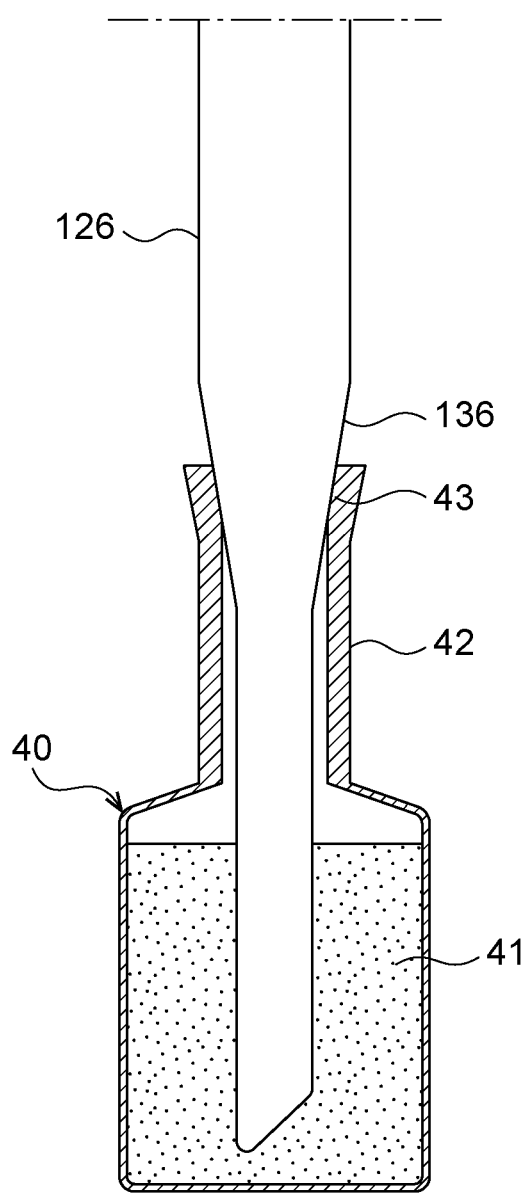
FIG. 11 is an enlarged cross-sectional view of the distal end of the spray head and another small clogging prevention container attached thereto.

As illustrated in FIG. 11, a tapered portion (engaging portion) 136 whose outer diameter gradually decreases toward the distal side may be formed at the distal portion 25 of the spray head or the distal portion of the extension 126, and a tapered portion (engaged portion) 43 having a shape corresponding to the container mouth 42 may be formed so that the distal end of the spray head or the distal end of the extension is reliably immersed in the solution 41 in a state where the tapered portion 136 of the spray head or the extension contacts the tapered portion 43 of the container mouth 42. In this case, the solution 41 can be prevented from leaking by the tapered portions 136 and 43 contacting each other. In this case, even when the spray head immersed in the container 40 and the container 40 are turned sideways, the solution does not leak. It is also desirable that the distal portion 25 of the spray head or extension 126 does not contact the bottom face of the container 40.

EXAMPLES

Materials, Instruments, Methods, and the Like

As a fibrin glue preparation, a dedicated spray set (corresponds to the "nebulizer" described above) of a 3 mL preparation of BOLHEAL (registered trademark) tissue adhesion (KM Biologics Co., Ltd.) was used. First, the dissolved BOLHEAL was drawn into a dedicated syringe using a BOLHEAL preparation set to assemble a spray set. The gas pressure of the sterile gas was set to 0.075 MPa, air was sent from the air line to the spray head, and 0.5 mL of each of the liquid medicines was sprayed by one time spraying. Three seconds after spraying, the air line was clamped and allowed to stand for 20 minutes. A maximum of five sprays were performed, and the spray state and the number of sprayable times were confirmed.

Example 1

Comparison of Effects of the Partition Wall Separating Two Liquid Spray Ports (Solution Ejection Ports) of the Liquid a and the Liquid B, and the Small Clogging Prevention Container Containing Physiological Saline Attached to the Spray Head Distal Portion Among the dedicated spray sets for BOLHEAL, the "end spray 32 cm straight type" has a long length to the extension distal end, and clogging is likely to occur. When spraying is stopped once and then sprayed again, clogging occurs with high probability. This time, the factor has been successfully identified. The two types of liquids of fibrin glue have greatly different viscosities, and when the two types of liquids are attempted to be sprayed in equal amounts, there is a difference in liquid passage resistance for the respective flow paths. The difference in liquid passage resistance leads to a difference in syringe internal pressure, and the difference in pressure is eliminated after the spraying is stopped. However, for the purpose of uniform spraying of both liquids, the pushing of both syringes are fixed so as to be aligned at the same height, and the elimination of the difference in pressure proceeds by ejection of the liquid medicine from the syringe having a high pressure and suction from the nozzle to the syringe having a low pressure. Specifically, in the fibrin glue, the fibrinogen solvent having high viscosity is pushed out from the syringe, and the thrombin solvent having low viscosity is sucked up into the syringe. At this time, it has been found that the fibrinogen solvent once ejected to the distal end of the extension is sucked up by the thrombin solvent tube, whereby the thrombin solvent tube is blocked. In order to prevent the sucking, the present inventors have invented a nebulizer in which a partition wall separating ejection ports of both liquids is provided at a distal end of an extension. In addition, the present inventors have invented a clogging prevention container to be attached to a spray head filled with physiological saline for the purpose of preventing clogging due to precipitation of a protein of a dried liquid medicine or cleaning a liquid medicine remaining at a distal end of the spray head. This time, for the purpose of confirming the clogging prevention effect of both mechanisms (presence or absence of the partition wall, use/non-use of clogging container), a comparative examination was carried out by allowing the nebulizer to stand for 20 minutes after spraying and checking the number of sprayable times up to 5 times.

[Group Setting]

Figure 12:
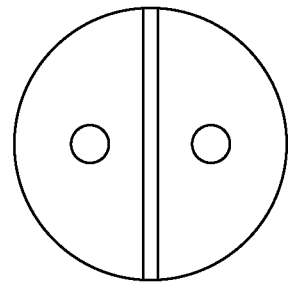
FIG. 12 is a front view of the spray head distal portion without a protective wall (partition wall guard)
Figure 13A:
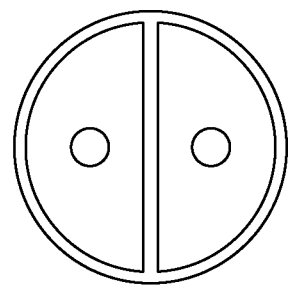
FIGS. 13(a) to 13(c) are front views of a spray head distal portion having a partition wall and a protective wall (partition wall guard)
Figure 13B:
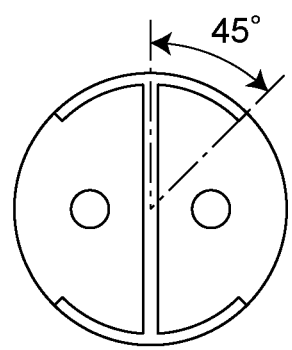
Figure 13C:
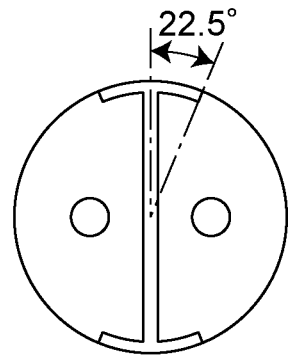

Group A (with partition wall [see FIG. 12], use of clogging prevention container): a group in which spraying is performed with a spray head having a partition wall with a height of 1 mm between two liquid spray ports of the BOLHEAL end spray 32 cm straight type tip, and the tip is placed in a container filled with 10 mL of physiological saline and allowed to stand
- Group B (with partition wall, clogging prevention container is not used): a group in which spraying is performed with a spray head having a partition wall with a height of 1 mm between two liquid spray ports of the BOLHEAL end spray 32 cm straight type tip, and the spray head is allowed to stand as it is
- Group C (without partition wall, use of clogging prevention container): a group in which spraying is performed with the BOLHEAL end spray 32 cm straight type as it is, and the tip was placed in a container filled with 10 mL of physiological saline and allowed to stand
- Group D (without partition wall, no use of clogging prevention container): a group in which spraying is performed with the BOLHEAL end spray 32 cm straight type as it is and the spray head is allowed to stand as it is (control group)

In groups A to D, the amount of protrusion (height) of the tube distal end from the spray head was 1 mm.

[Results]

The test was performed using 5 end spray 32 cm straight types (3 types for the control group of Group D), and the following results were obtained.

| Group | Results |
|---|---|
| Group A (with partition wall/use of container) | Five times spraying was successfully performed with all five sprays. |
| Group B (with partition wall/no use of container) | Three or four times spraying was not successfully performed with all five sprays. |

-continued

| Group | Results |
|---|---|
| Group C (without partition wall/use of container) | Five times spraying was successfully performed with one spray, but two times spraying was not successfully performed with the remaining four sprays |
| Group D (without partition wall/no use of container) | Two times spraying was not successfully performed with one spray, and only one time spraying was successfully performed with the remaining two sprays |

As described above, the clogging prevention effect by the partition wall at the distal end of the spray head, and by placing the distal end of the spray head in the clogging prevention container filled with physiological saline and is allowed to stand was confirmed. Specifically, it was considered that the effect of the partition wall had a larger contribution.

Example 2

Comparison of Clogging Prevention Effect of Distal Portion Shape of Spray Head for Introducing Partition Wall Separating Two Liquid Spray Ports (Solution Ejection Port) of the Liquid A and the Liquid B As in Example 1, among the dedicated spray sets for BOLHEAL, the "end spray 32 cm straight type" has a long length to the extension distal end and is easily clogged, and thus is basically recommended to be used only once. In Example 1, the clogging prevention effect by the partition wall and by placing the distal end of the spray head in the clogging prevention container filled with physiological saline and allowing the spray head to stand was confirm, and in particular, the effect of the partition wall had a greater contribution. On the other hand, since it is considered that the influence of damaging the tissue is increased by the contact of the partition wall with the target tissue, the shapes of the distal end of the spray head were compared and examined.

[Group Setting]

- Group 1: a group in which a partition wall with a height of 1 mm is installed between two liquid spray ports of the BOLHEAL end spray 32 cm straight type tip, spraying is performed with a spray head having a partition wall guard (corresponding to a "protective wall") with a height of 1 mm on the entire circumference along an edge of a distal end face, and a distal end of the spray head is placed in a container filled with 10 mL of physiological saline and allowed to stand (see FIG. 13(*a*))
- Group 2: a group in which a partition wall with a height of 1 mm is installed between two liquid spray ports of the BOLHEAL end spray 32 cm straight type tip, spraying is performed with a spray head having a partition wall guard with a height of 1 mm in a region of 45 degrees from both ends of the partition wall, and the tip is placed in a container filled with 10 mL of physiological saline and allowed to stand (see FIG. 13(*b*))
- Group 3: a group in which a partition wall with a height of 1 mm is installed between two liquid spray ports of the BOLHEAL end spray 32 cm straight type tip, spraying is performed with a spray head having a partition wall guard with a height of 1 mm in a region of 22.5 degrees from both ends of the partition wall, and the tip is placed in a container filled with 10 mL of physiological saline and allowed to stand (see FIG. 13(c))

In Group 1 to Group 3, the amount of protrusion (height) of the tube distal end from the spray head was 1 mm.

[Results]

When whether spraying was successful was confirmed using three end spray 32 cm straight types, the following results were obtained.

| Group | Results |
|---|---|
| Group 1 (with partition wall/partition wall guard disposed on entire circumference) | Four times spraying was successfully performed with one spray, but two times spraying was not successfully performed with the remaining two sprays. |
| Group 2 (with partition wall/partition wall guard disposed in 45 degree region) | Four times spraying was successfully performed with one spray, but four times spraying was not successfully performed with the remaining two sprays. |
| Group 3 (with partition wall/partition wall guard disposed in 22.5 degree region) | Five times spraying was successfully performed with two sprays, but five times spraying was not successfully performed with the remaining one spray. |

From the above, it was confirmed that Group 3 had the spray head distal end shape having a high clogging prevention effect. When the edible dye blue (Blue No. 1, KENIS LIMITED) was added to the fibrinogen liquid and the edible dye red (Red No. 102, KENIS LIMITED) was added to the thrombin liquid of BOLHEAL so as to ensure the visibility, and the height of the partition wall between the two liquid spray ports of the spray tip of Group 3 was changed from 1 mm to 2 mm, the spray state and the number of sprayable times were not affected, but spraying was not successfully performed with the partition wall with a height of 3 mm, which was a defect. The height of the partition wall was considered to be suitably in a range of 1 to 2 mm.

Example 3

Comparison of Tissue Friendliness of Distal Portion Shape of Spray Head for Introduction of Partition Wall Separating Two Liquid Spray Ports (Solution Ejection Ports) of the Liquid A and the Liquid B Difference in contact injury of the target tissue due to difference in the distal portion geometry of the spray head was compared. As an evaluation method, the spray distal end portion attached to the tip of the push-pull gauge was pressed against the fixed pig liver with an electric stand (50 mm/min), and the maximum pressing force (N: Newton) until the film or the parenchyma of the pig liver was damaged was recorded.

[Group Setting]

Group 4: a group in which a partition wall with a height of 1 mm is installed between two liquid spray ports of the BOLHEAL end spray 32 cm straight type tip, spraying is performed with a spray head having a partition wall guard (corresponding to a "protective wall") with a height of 1 mm on the entire circumference along the edge of the distal end face, and the tip is placed in a container filled with 10 mL of physiological saline and allowed to stand (see FIG. 13(a))

Group 5: a group in which a partition wall with a height of 1 mm is installed between two liquid spray ports of the BOLHEAL end spray 32 cm straight type tip, spraying is performed with a spray head having a partition wall guard with a height of 1 mm in a region of 45 degrees from both ends of the partition wall, and the tip is placed in a container filled with 10 mL of physiological saline and allowed to stand (see FIG. 13(b))

Group 6: a group in which a partition wall with a height of 1 mm is installed between two liquid spray ports of the BOLHEAL end spray 32 cm straight type tip, spraying is performed with a spray head having a partition wall guard with a height of 1 mm in a region of 22.5 degrees from both ends of the partition wall, and the tip is placed in a container filled with 10 mL of physiological saline and allowed to stand (see FIG. 13(c))

Group 7: a group in which spraying is performed with a spray head having a partition wall with a height of 1 mm between two liquid spray ports of the BOLHEAL end spray 32 cm straight type tip, and the tip is placed in a container filled with 10 mL of physiological saline and allowed to stand (see FIG. 12)

In Group 4 to Group 7, the amount of protrusion (height) of the tube distal end from the spray head was 1 mm.

[Results]

The test was performed using five end spray 32 cm straight types, and the following results were obtained (unit of numerical value: N).

| Group | 1 | 2 | 3 | 4 | 5 | Mean ± SD |
|---|---|---|---|---|---|---|
| Group 4 (with partition wall/partition wall guard disposed on entire circumference) | 11.74 | 11.23 | 12.28 | 12.18 | 13.86 | 12.26 ± 0.99 |
| Group 5 (with partition wall/partition wall guard disposed in 45 degree region) | 12.10 | 9.73 | 8.67 | 10.33 | 9.35 | 10.04 ± 1.30 |
| Group 6 (with partition wall/partition wall guard disposed in 22.5 degree region) | 10.59 | 11.47 | 10.16 | 9.70 | 11.48 | 10.68 ± 0.79 |
| Group 7 (with partition wall/without partition wall guard) | 1.67 | 1.73 | 3.31 | 1.87 | 3.86 | 2.49 ± 1.02 |

From the above, with respect to the maximum pressing force in which damage was observed in the tissue, the effect of Group 4 to 6 was 4 times or more higher than that of Group 7 having only the partition wall. It was confirmed that among them, Group 4 was the most excellent in the tissue friendliness, and there was no large difference between Group 5 and Group 6 whose tissue friendliness was maintained as compared with Group 7 having only the partition wall.

Example 4

Comparison of Size of Small Clogging Prevention Container Containing Physiological Saline Attached to Distal Portion of Spray Head The clogging prevention effect was compared by changing the volume (solution storage amount) of the clogging prevention container.

[Group Setting]

- Group 8: a group in which a partition wall with a height of 1 mm is installed between two liquid spray ports of the BOLHEAL end spray 32 cm straight type tip, spraying is performed with a spray head having a partition wall guard with a height of 1 mm in a region of 22.5 degrees from both ends of the partition wall, and the tip is placed in a container filled with 10 mL of physiological saline and allowed to stand (see FIG. 13(a))
- Group 9: a group in which a partition wall with a height of 1 mm is installed between two liquid spray ports of the BOLHEAL end spray 32 cm straight type tip, spraying is performed with a spray head having a partition wall guard with a height of 1 mm in a region of 22.5 degrees from both ends of the partition wall, and the tip is placed in a container filled with 5 mL of physiological saline and allowed to stand (see FIG. 13(c))
- Group 10: a group in which a partition wall with a height of 1 mm is installed between two liquid spray ports of the BOLHEAL end spray 32 cm straight type tip, spraying is performed with a spray head having a partition wall guard with a height of 1 mm in a region of 22.5 degrees from both ends of the partition wall, and the tip is placed in a container filled with 3 mL of physiological saline and allowed to stand (see FIG. 13(c))
- Group 11: a group in which a partition wall with a height of 1 mm is installed between two liquid spray ports of the BOLHEAL end spray 32 cm straight type tip, spraying is performed with a spray head having a partition wall guard with a height of 1 mm in a region of 22.5 degrees from both ends of the partition wall, and the tip is placed in a container filled with 1 mL of physiological saline and allowed to stand (see FIG. 13(c))

In Group 8 to Group 11, the amount of protrusion (height) of the tube distal end from the spray head was 1 mm.

[Results]

The test was performed using three end spray 32 cm straight types, and the following results were obtained.

| Group | Results |
| --- | --- |
| Group 8 (10 mL container) | Five times spraying was successfully performed with two sprays, but five times spraying was not successfully performed with the remaining one spray. |
| Group 9 (5 mL containers) | Five times spraying was successfully performed with one spray, but five times spraying was not successfully performed with the remaining two sprays. |
| Group 10 (3 mL container) | Five times spraying was successfully performed with three sprays. |
| Group 11 (1 mL container) | Two times spraying was successfully performed with two sprays, but two times spraying was not successfully performed with the remaining one spray. |

As illustrated in the table, four to five times spraying was successfully performed in Groups 8 to 10. On the other hand, it was confirmed that when the container was reduced to 1 mL of Group 11, a plurality of times of spraying was not successfully performed. From this, it was considered that the size of the small clogging prevention container containing physiological saline is preferably 3 mL or more for a plurality of times of spraying.

Example 5

Comparison of Clogging Prevention Effect Using Applicator with Short Extension of Spray Head Using the applicator in which the length of the extension of the spray head was short, the clogging prevention effect due to the difference in the presence or absence of the partition wall and the presence or absence of the clogging prevention container was compared.

[Test Method]

The same procedure as in Example 1 was carried out except that the length of the extension of the spray head was 3 cm.

[Group Setting]

- Group E (with partition wall [see FIG. 12], use of clogging prevention container): a group in which the BOLHEAL end spray has a length of 3 cm, spraying is performed with a spray head having a partition wall with a height of 1 mm installed between two liquid spray ports, and the tip was placed in a container filled with 10 mL of physiological saline and allowed to stand
- Group F (with partition wall, no use of clogging prevention container): a group in which the BOLHEAL end spray has a length of 3 cm, spraying is performed with a spray head having a partition wall with a height of 1 mm between two liquid spray ports, and the spray head is allowed to stand as it is
- Group G (without partition wall, use of clogging prevention container): a group in which the BOLHEAL end spray has a length of 3 cm, spraying is performed as it is, and the tip was placed in a container filled with 10 mL of physiological saline and allowed to stand
- Group H (without partition wall, no use of clogging prevention container): a group in which the BOLHEAL end spray has a length of 3 cm, spraying is performed as it is, and the spray head is allowed to stand as it is (control group)

In Group E to Group H, the amount of protrusion (height) of the tube distal end from the spray head was 1 mm.

[Results]

The test was performed using 5 sprays for Group E and 3 sprays for other Groups (length: 3 cm), and the following results were obtained.

| Group | Results |
| --- | --- |
| Group E (with partition wall/use of container) | Five times spraying was successfully performed with all five sprays. |

-continued

| Group | Results |
|---|---|
| Group F (with partition wall/no use of container) | Five times spraying was successfully performed with one spray, but four times spraying was not successfully performed with the remaining two sprays. |
| Group G (without partition wall/use of container) | Five times spraying was successfully performed with two sprays, but four times spraying was not successfully performed with the remaining one spray. |
| Group H (without partition wall/no use of container) | Two or three times spraying was not successfully performed with all three sprays. |

As described above, in the case of the applicator having a short spray head, the clogging prevention effect by the partition wall of the distal end and by placing the distal end of the spray head in the clogging prevention container filled with physiological saline and is allowed to stand was confirmed. In addition, a certain effect could be confirmed even when any one of the partition wall and the clogging prevention container was used.

Example 6

Prototype Applicator Spray Tip Shape and Small Clogging Prevention Container Containing Physiological Saline Attached to Tip From the contents found in Examples 1 to 5, a prototype was manufactured, and five times spraying was successfully confirmed.

What is claimed is:

1. A biological tissue adhesive nebulizer, comprising:
a first tube for injecting a first solution containing a first component;
a second tube for injecting a second solution containing a second component that promotes clot formation of the first component, the first solution injected from the first tube and the second solution injected from the second tube being mixed to generate and spray a biological tissue adhesive, and
a spray head having a hollow housing,
the housing having
a center axis extending in a first direction (X) from a proximal side to a distal side of the housing, and
a proximal portion and a cylindrical distal portion;
the distal portion having a first through hole and a second through hole, the first through hole and the second through hole extending in the first direction (X) and spaced away from each other in a second direction (Y) orthogonal to the first direction (X) to communicate between an inside and an outside of the housing;
the first tube and the second tube being inserted through the first through hole and the second through hole, respectively, to protrude from an end surface of the distal portion, and
the end surface having
a partition extending across the end surface between the first through hole and the second through hole, in a third direction orthogonal both to the first direction (X) and the second direction (Y); and
a first pair of protective walls provided at one end of the partition to extend in opposite directions away from the partition and along a peripheral edge of the end surface.

2. The biological tissue adhesive nebulizer of claim 1, wherein the end surface further having a second pair of protective walls provided at opposite end of the partition to extend in opposite directions away from the partition and along the peripheral edge of the end surface.

3. The biological tissue adhesive nebulizer of claim 1, wherein the end surface extends orthogonally to the central axis.

4. The biological tissue adhesive nebulizer of claim 1, wherein the end surface extends obliquely to the central axis.

5. The biological tissue adhesive nebulizer of claim 1, wherein
an inner diameter of the first through hole is larger than an outer diameter of the first tube, and a first gas injection hole is formed around the first tube inserted into the first through hole, wherein
an inner diameter of the second through hole is larger than an outer diameter of the second tube, and a second gas injection hole is formed around the second tube inserted into the second through hole, wherein
a sterile gas supply pipe is connected to the inside of the housing, and wherein
a sterile gas supplied from the sterile gas supply pipe to the inside of the housing is injected from the first gas injection hole formed between an inner face of the first through hole and an outer face of the first tube and the second gas injection hole formed between an inner face of the second through hole and an outer face of the second tube.

6. A container for use with the biological tissue adhesive nebulizer according to claim 1, wherein the container has a mouth shape detachably attachable to a terminal portion of the housing, and accommodates physiological saline therein.

7. The container of claim 6, the container being for use with a biological tissue adhesive nebulizer, wherein the container includes an engaged portion with which an engaging portion formed in the biological tissue adhesive nebulizer is engaged so that a distal portion of the biological tissue adhesive nebulizer does not come into contact with a bottom face of the container.

* * * * *